US006492537B2

(12) United States Patent
Foglia et al.

(10) Patent No.: US 6,492,537 B2
(45) Date of Patent: Dec. 10, 2002

(54) SOLVENT FRACTIONATION OF MENHADEN OIL AND PARTIALLY HYDROGENATED MENHADEN OIL FOR MAKING LIPID COMPOSITIONS ENRICHED IN UNSATURATED FATTY ACID-CONTAINING TRIACYLGLYCEROLS

(75) Inventors: Thomas A. Foglia, Lafayette Hill, PA (US); Ki-Teak Lee, Taejon (KR)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 87 days.

(21) Appl. No.: 09/785,334

(22) Filed: Feb. 20, 2001

(65) Prior Publication Data

US 2002/0156306 A1 Oct. 24, 2002

(51) Int. Cl.[7] .................................................. C07C 1/00

(52) U.S. Cl. ............................ 554/20; 554/8; 426/417; 426/425; 426/429; 426/478

(58) Field of Search ................................ 424/417, 425, 424/429, 478; 554/8, 20

(56) References Cited

U.S. PATENT DOCUMENTS 5,198,250 A 3/1993 Brillhart ........................ 426/2

OTHER PUBLICATIONS

Chen et al., Journal of the American Oil Chemists' Society, vol. 77, No. 4, pp. 425–428, 2000.*

Bockisch, M., *Modification of fats and oils,* Fats and Oils Handbook, AOCS Press, Champaign, IL (1998), Ch. 6, pp. 446–612.

Brockerhoff, H., et al., *Positional distribution of fatty acids in triglycerides of animal depot fats*, Biochima et Biophysica Acta., vol. 116 (1966), pp. 67–72.

Christie, W.W., HPLC and Lipids, Pergamon Press, New York (1987), pp. 42–102.

Emken, E.A., *Do trans acids have adverse health consequences*?, Health Effects of Dietary Fatty Acids, G.J. Nelson, ed., AOCS Press, Champaign, IL (1991), pp. 245–263.

Foglia, T.A., et al., *Enzymatic interesterification of tallow-sunflower oil mixtures, J. Am. Oil Chem. Soc.,* vol. 70(3) (1993), pp. 281–285.

Grundy, S.M., *Disorders of lipids and lipoproteins*, Internal Medicine, Stein, ed. (2nd edition 1987), pp. 2035–2046.

Halliwell, B., et al., *Lipid peroxidation: A radical chain reaction*, Free Radicals in Biology and Medicine (2nd ed. 1989), Ch. 4, pp. 188–276.

Lee, I., et al., *Use of branched–chain esters to reduce the crystallization temperature of biodiesel*, J. Am. Oil Chem. Soc., vol. 72(10) (1995), pp. 1155–1160.

Lee, K.–T., et al., *Structured lipids: Synthesis and applications*Food Rev. Int., vol. 14(1) (1998), pp. 17–34.

Manganaro, F., et al., *Acylglycerol structure of genetic varieties of peanut oils of varying atherogenic potential*, Lipids, vol. 16(7) (1981), pp. 508–517.

(List continued on next page.)

*Primary Examiner*—Deborah D. Carr
(74) *Attorney, Agent, or Firm*—M. Howard Silverstein; John D. Fado; G. Byron Stover

(57) ABSTRACT

Lipid compositions enriched in unsaturated fatty acid-containing triacylglycerols are made from menhaden oil (MO) and partially hydrogenated menhaden oil (PHMO) to provide a lipid composition containing enriched monounsaturated fatty acid esters (MUFAs) and polyunsaturated fatty acid esters (PUFAs).

36 Claims, 5 Drawing Sheets

OTHER PUBLICATIONS

Mattson, F.H., et al., *Comparison of effects of dietary saturated, mono–unsaturated, and polyunsaturated fatty acids on plasma and lipoproteins in man*, Journal of Lipid Research, vol. 26 (1985), pp. 194–202.

Nicolosi, R.J., et al., *Effect of dietary fat saturation on low density lipoprotein metabolism*, Health Effects of Dietary Fatty Acids, G.J. Nelson, ed., AOCS Press, Champaign, IL (1991), Ch. 7, pp. 77–82.

Rossell, J.B., *Fractionation of lauric oils*, J. Am. Oil Chem. Soc., vol. 62 (1985), pp. 385–390.

Spady, D.K., et al., *Dietary saturated triacylglycerols suppress heptic low–density lipoprotein receptor activity in the hamster*, Proc. Natl. Acad. Sci., vol. 82 (1985), pp. 4526–4530.

USDA Economic Research Service, *Livestock, Dairy and Poultry Situation and Outlook*, USDA Economic Research Service , Publication LDP–M–55, Jan. 26, 1999.

* cited by examiner

SOLVENT FRACTIONATION OF MENHADEN OIL AND PARTIALLY HYDROGENATED MENHADEN OIL FOR MAKING LIPID COMPOSITIONS ENRICHED IN UNSATURATED FATTY ACID-CONTAINING TRIACYLGLYCEROLS

FIELD OF THE INVENTION

The present invention pertains to enriched unsaturated fatty acid-containing triacylglycerols and a method of making them employing menhaden oil (MO) or partially hydrogenated menhaden oil (PHMO). In particular, the method involves the solvent fractionation of MO or PHMO to provide a lipid composition containing enriched amounts of unsaturated fatty acid esters (UFA or UFAs) including monounsaturated fatty acid esters (MUFA or MUFAs) and polyunsaturated fatty acid esters (PUFA or PUFAs).

BACKGROUND OF THE INVENTION

One established approach to reducing plasma cholesterol levels is to consume a large proportion of dietary triglycerides as polyunsaturated fatty acid (PUFA) derivatives. The most widely occurring dietary PUFA is linoleic acid (C18:2n-6, or 9,12-octadecadienoic acid), which constitutes more than half of the fatty acid triglycerides of corn, soy, and safflower vegetable oils. The cholesterol lowering ability of PUFAs is believed to result from increased LDL receptor activity. See Spady & Dietschy, Proc. Nat. Acad. Sci. USA, Vol. 82 (1985), pp.4526–4530. This well established lowering of plasma LDL cholesterol concentration when PUFAs are substituted for dietary saturated fatty acids (hereinafter SFA or SFAs) provides the rationale for the widespread substitution of a variety of vegetable oils for animal fats in cooking and food formulations. The American Heart Association in its Phase I and Phase II Recommended Diets has approved the use of PUFAs as part of a large scale dietary modification for the purpose of lowering cholesterol levels in the general population. See, e.g., S. M. Grundy, Disorders of Lipids and Lipoprotein, in *Internal Medicine,* Stein, ed., (2nd ed. 1987), pp. 2035–2046.

However, PUFAs have significant deleterious health consequences as well as beneficial ones. Several negative effects of PUFAs may be ascribed to their increased rate of reaction via free-radical mechanisms. See, e.g., B. Halliwell and J. Gutteridge, "Lipid Peroxidation," Ch. 4 in *Free Radicals in Biology and Medicine* (2d ed. 1989). PUFAs usually have two vinylic groups separated by a methylene carbon, as is exemplified by the 9,12 diene structure of linoleic acid. Their susceptibility to peroxidation and cross-linking reactions implicates PUFAs in several undesirable processes such as tissue aging, tumorigenesis and lowering the level of beneficial HDL cholesterol as well as the level of harmful LDL cholesterol.

Monounsaturated fatty acids, such as oleic acid (C18:1n-9) or (cis-9-octadecenoic acid), are known to reduce blood cholesterol levels in non-hypertriglyceridemic individuals (F. H. Mattson and S. M. Grundy, J. Lipid Res., 26, 1985, pp. 94–202). Among vegetable oils, those of olive, peanut, rapeseed and canola have been identified as being rich sources of MUFA, with the latter type fatty acids constituting from 50% to 80% of their fatty acid composition. Because of the importance placed on dietary MUFA, it has been recommended that MUFA intake be as high as half of the total recommended dietary intake of calories from fat (30%) as a means for reducing the risk of coronary artery disease (R. J. Nicolosi, A. F. Stucchi and J. Loscalzo,Chapter 7 in *Health Effects of Dietary Fatty Acids,* G. J. Nelson, ed., AOCS Press, Champaign, Ill., 1991, pp. 77–82; M. Bockisch in *Fats and Oils Handbook,* AOCS Press, Champaign, Ill. 1998; K.-T. Lee and C. C. Akoh, Food Rev. Int., 14, 1998, pp. 17–34).

Although scientifically based claims of health benefits derived from dietary MUFAs previously have been asserted for oleic acid, other monounsaturated fatty acids also occur naturally. The most common are 11-eicosenoic acid (C20:1n-9) and 13-docosenoic acid (C22:1n-9), both of which are found in high levels in some oilseed plants such as jojoba and rapeseed. The shorter chain MUFA 9-palmitoleic acid (C16:1n-7) occurs as a minor component (ca. 2%) in olive and cottonseed oils and in trace amounts in a few other commercially available vegetable oils. Palmitoleic acid occurs in somewhat high amounts in animal fat triglycerides such as lard and tallow (up to 5%) and in still higher levels in some fish oils such as sardine oil. The next lower homologue, myristoleic (9-tetradecenoic) acid (C14:1n-5), occurs in minor amounts in animal fat and in butter. The even lower homologue, lauroleic (9-dodecenoic) acid (C12:1n-3), occurs rarely and in small amounts in natural sources.

Several animal fats contain short chain MUFAs in sufficiently high proportions to make them good starting materials for formulating desirable compositions. Chicken and turkey fats, beef tallow, and foot bone oil triglycerides contain C16:1n-7 in amounts of about 4–6% by weight. Some fish oils such as sardine and menhaden may contain as much as 10–16% C16:1n-7. Whale oil is reported to contain above 13% C16:1n-7, and the now unavailable sperm whale oil contained up to 26%. However, these fats and oils as rendered from the natural sources contain undesirably large relative proportions of the long chain fatty acids of the series C20:x and above. The more saturated and higher melting members C20:0, C20:1 and C22:0 have been reported to contribute to the high atherogenicity of peanut oil, a phenomenon comprehensible in light of the teachings of this patent. See F. Manganaro, et al., Lipids, 16, 1981, pp. 508–517. The polyunsaturated and lower melting members C20:2, C20:3, C20:4, C20:5, C22:2, C22:3, C22:4, C22:5, and C22:6 are non-atherogenic or even cardioprotective, but are highly sensitive to free radical oxidation and cross linking reactions because of their polyunsaturation.

The principal source of a dietary vegetable oil which contains appreciable amounts of C16:1n-7 is macadamia nuts. The two species, integrifolia and tetrafolia, contain C16:1n-7 in amounts ranging from 16 to 25% (w/w) of the fatty acids in the oil. However, both also contain about 2% to 4% C20 fatty acids. In addition, the other fatty acids of macadamia nut oil are closely similar in both identity and quantity to those present in olive oil.

Similarly, some natural fats and oils are acceptable starting materials from which to manufacture desirable compositions, that is , an oil enriched in the other selected short chain MUFAs. For example, tallow contains about 0.5% C14:1n-5. It also contains about 1% or more C20 to C22 fatty acids. Butterfat contains very large proportions, up to 3%, of C14:1n-5. However, butterfat has other lipid components, including a large fraction of C4 to C10 fatty acids. The latter are metabolized by a quite different pathway from the C12 and longer fatty acids. Butterfat also contains greater than 2% C20 fatty acids.

In U.S. Pat. No. 5,198,250, food and pharmaceutical compositions containing short chain monounsaturated fatty acids (MUFAs) and methods of using them are disclosed. In particular, as set forth in detail in that patent, MUFA compositions were formulated to produce beneficial improvements in the metabolic processing of lipids or glucose in animals to which the compositions of matter are regularly administered. Beneficial improvements in the metabolic processing of lipids are evidenced by different effects in various tissues. Generally, the metabolic processing of lipids may include any or all steps in the metabolic pathways which include, in part, lipid uptake from dietary sources, hydrolysis, esterification of fatty acids to produce other lipid species, packaging of lipids into lipoproteins, lipid transport, lipid storage in tissues, lipid or lipoprotein cellular uptake, lipid synthesis, enzymatic modification and catabolism, and pathological lipid deposition in arteries, liver, heart and in adipose tissue. As set forth in the disclosure of that patent in detail, regular or systematic administration of the formulated MUFA compositions provide beneficial improvements in metabolic processing.

In 1998, chicken was the most produced and consumed meat in the United States (USDA 1999, publication #LDP-M-55, Economic Research Service, Washington, D.C.). Despite its production and ready availability as a coproduct of chicken production, chicken fat, unlike beef tallow, is usually not used separately in other food or non-food uses. However, animal fats, in general, are of dietary concern because of their relatively high long-chain (C16 and C18 carbon atoms) saturated fatty acid (SFA) content. Chicken fat can be considered a source of MUFA since they constitute 45–50% of chicken fat fatty acids, while tallow contains only 30–40% MUFA (H. Brockerhoff, R. J. Hoyle and N. Wolmark, Biochem. Biophys. Acta, 116, 1966, pp. 67–72; M. Bockisch, in *Fats and Oils Handbook,* AOCS Press, Champaign, Ill. 1998).

In brief, MUFAs selected from the group composed of palmitoleic acid (C16:1) and its positional isomers, myristoleic (tetradecenoic) acid (C14:1) and its positional isomers and lauroleic (dodecenoic) acid (C12:1), or their mixtures, whether as free acids, salts or esters thereof, are known to provide improvements in the metabolic processing of lipids. The beneficial health effects of the n-3 class of PUFAs, such as 5,8,11,14,17-eicosapentaenoic acid (EPA) and 4,7,10,13, 16,19-docosahexaenoic acid (DHA), are well documented. However, natural sources for such MUFAs, such as macadamia nut oil, are in limited supply. Also, natural compositions containing enriched n-3 PUFAs are needed. In order to satisfy the demands for MUFAs and PUFAs, improved methods are needed. Furthermore, new lipid compositions of UFAs containing PUFAs and MUFAs are needed.

SUMMARY OF THE INVENTION

This invention is directed to a method of making a lipid composition enriched in unsaturated fatty acid esters from menhaden oil (MO) and partially hydrogenated menhaden oil (PHMO). According to the method, MO or PHMO is solvent fractionated to produce lipid fractions that are enriched in unsaturated fatty acid-containing triacylglycerols. The fractionated lipid composition has an increased amount of unsaturated fatty acid esters and a decreased amount of saturated fatty acid esters compared to their original amounts in the MO or PHMO.

According to one preferred method of the invention, PHMO is solvent fractionated with a solvent, such as acetone, and the fractionation is conducted at a low temperature, preferably below ambient or room temperature, or below the range of 0° C. to −15° C., and, more preferably, in a range of about −18° C. to about −40° C. In another form of the method, the oil is liquified and then dry-fractionated over a temperature range of about −10° C. to about 35° C. during which time liquid and solid phases are formed. In the case of MO, dry fractionation is conducted at about −10° C., whereas with PHMO, the dry fractionation temperature is about 30° C. The separated liquid phase is then solvent fractionated with a suitable solvent, such as acetone, at low temperatures on the order of about 0° C. to about −40° C.

The unsaturated fatty acid-containing triacylglycerols enriched fractions produced by the method have significantly increased amounts of PUFAs and MUFAs. For instance, solvent fractionations at about −18° to about −38° C. produced lipid compositions having about 18% to about 32% by weight more UFAs compared to the original amounts of UFAs in the MO or PHMO. In contrast, saturated fatty acids (SFAs) in the solvent fractionated lipids decreased to about 7% to about 31% by weight of the original SFAs present in the MO or PHMO. In general, the UFAs increased about 5% to about 32% by weight and SFAs decreased about 7% to about 31% by weight for liquid and solid fractions for MO and PHMO. Correspondingly, the MUFAs in the fractionated lipid compositions increased about 0.5% to about 24% by weight of their original amounts; whereas the PUFAs increased about 3% to about 40% by weight for both MO and PHMO, and the SFAs decreased about 5% to about 50% by weight of their original amounts, and the eicosapentaenoic (EPA) and docosahexaenoic (DHA) classes increased about 5% to about 18% by weight of their original amounts.

When the two-step process is used, separation of a liquid phase of the MO or PHMO is required by dry fractionation at ambient temperatures, preferably a range of about −10° C. to 35° C., prior to solvent fractionation. The two-step process employs less solvent in the solvent fractionation step. MO did not give an isolatable (<2%) solid fraction above 0° C. or a liquid fraction below −10° C. Similarly PHMO remained mostly liquid above 31° C. and solid below 18° C.

In summary, novel lipid compositions are produced by the method of this invention. These compositions provide a number of advantages. For example, the content of the PUFAs, MUFAs and EPA and DHA classes in the lipid compositions are increased with a significant decrease of SFAs. An increase of the ratio of the unsaturated to the saturated fatty acids is also provided. The method offers an overall natural product for human consumption to facilitate the metabolic processing of lipids and avoid unwanted lipid deposits.

Other benefits and advantages of this invention will be further understood with reference to the following detailed description and examples.

Regression plot of triacylglycerol partition numbers (PN) versus retention times for standard triacylglycerol mixture.

Figure 3:
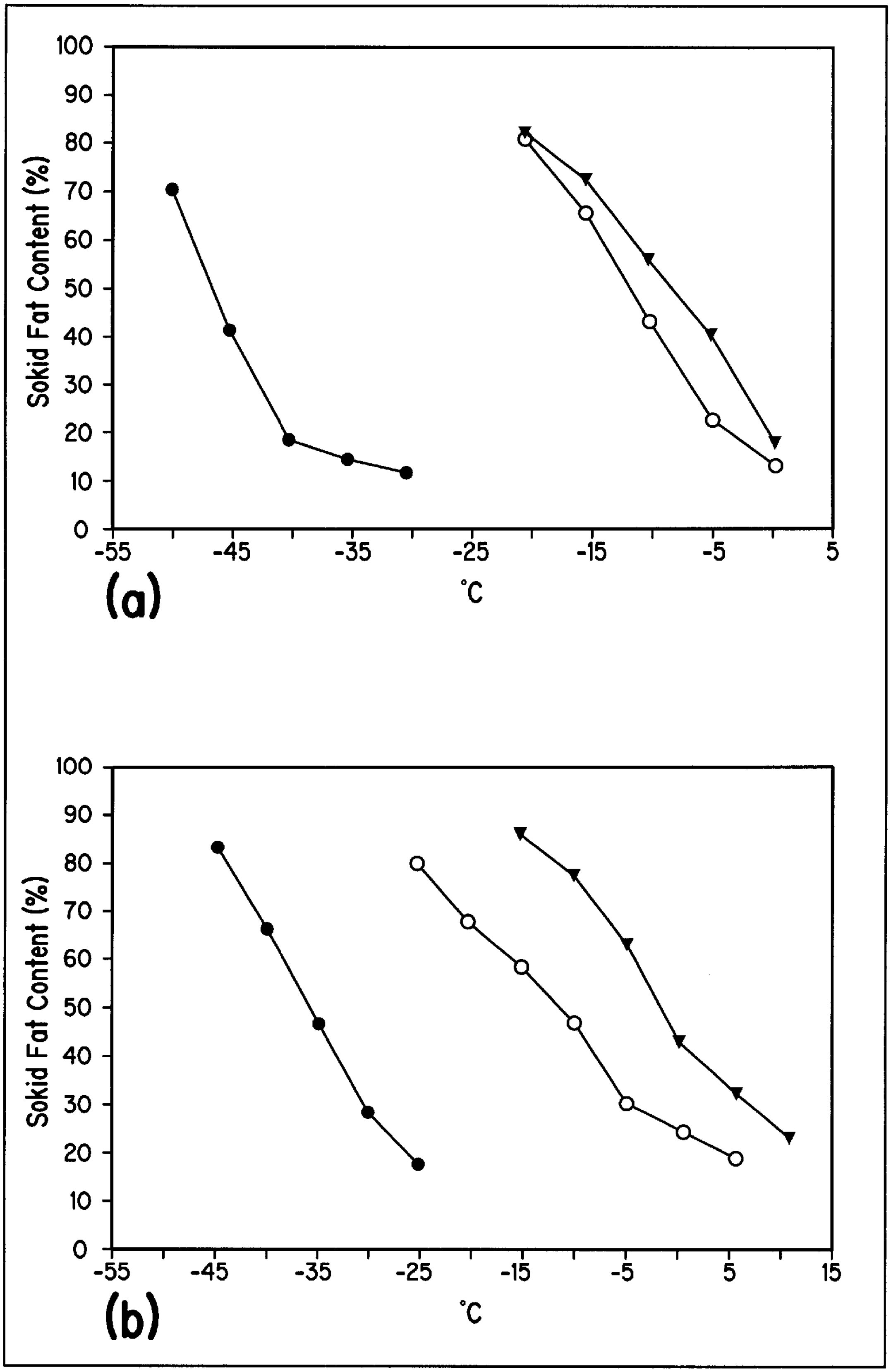

FIG. 3. Differential scanning calorimetry (DSC) solid fat content (%) curves for: (a) menhaden oil (MO, o) and the liquid (ρ) and solid fractions (▼) obtained from MO by acetone fractionation at −38° C.; and (b) partially hydrogenated menhaden oil (PHMO, o) and the liquid (ρ) and solid (▼) fractions obtained from PHMO by acetone fractionation at −38° C.

Figure 4:
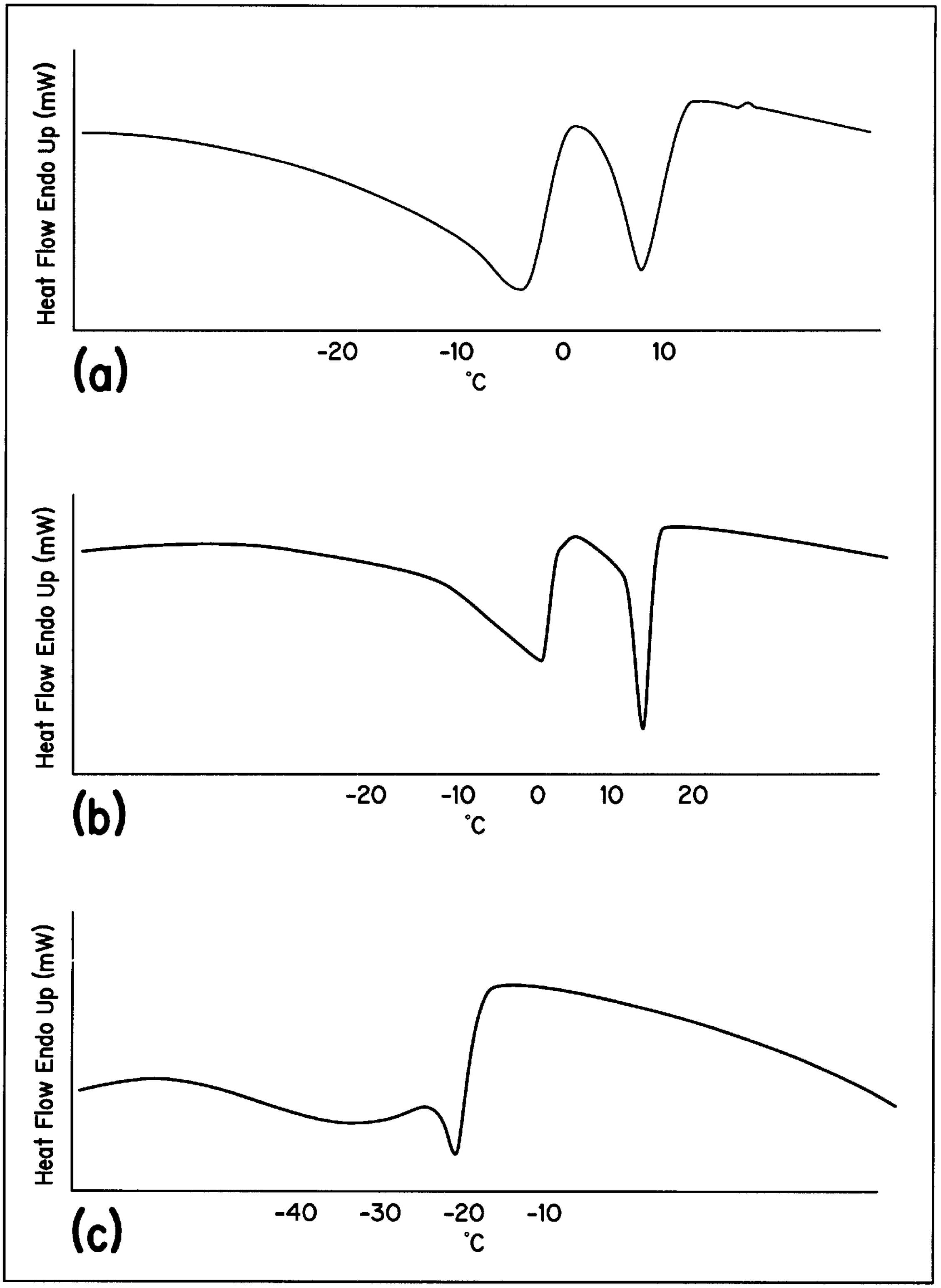

FIG. 4. DSC cooling curves (exotherm) for (a) menhaden oil (MO), (b) solid fraction, and (c) liquid fraction obtained from MO by acetone fractionation at −38° C.

Figure 5:
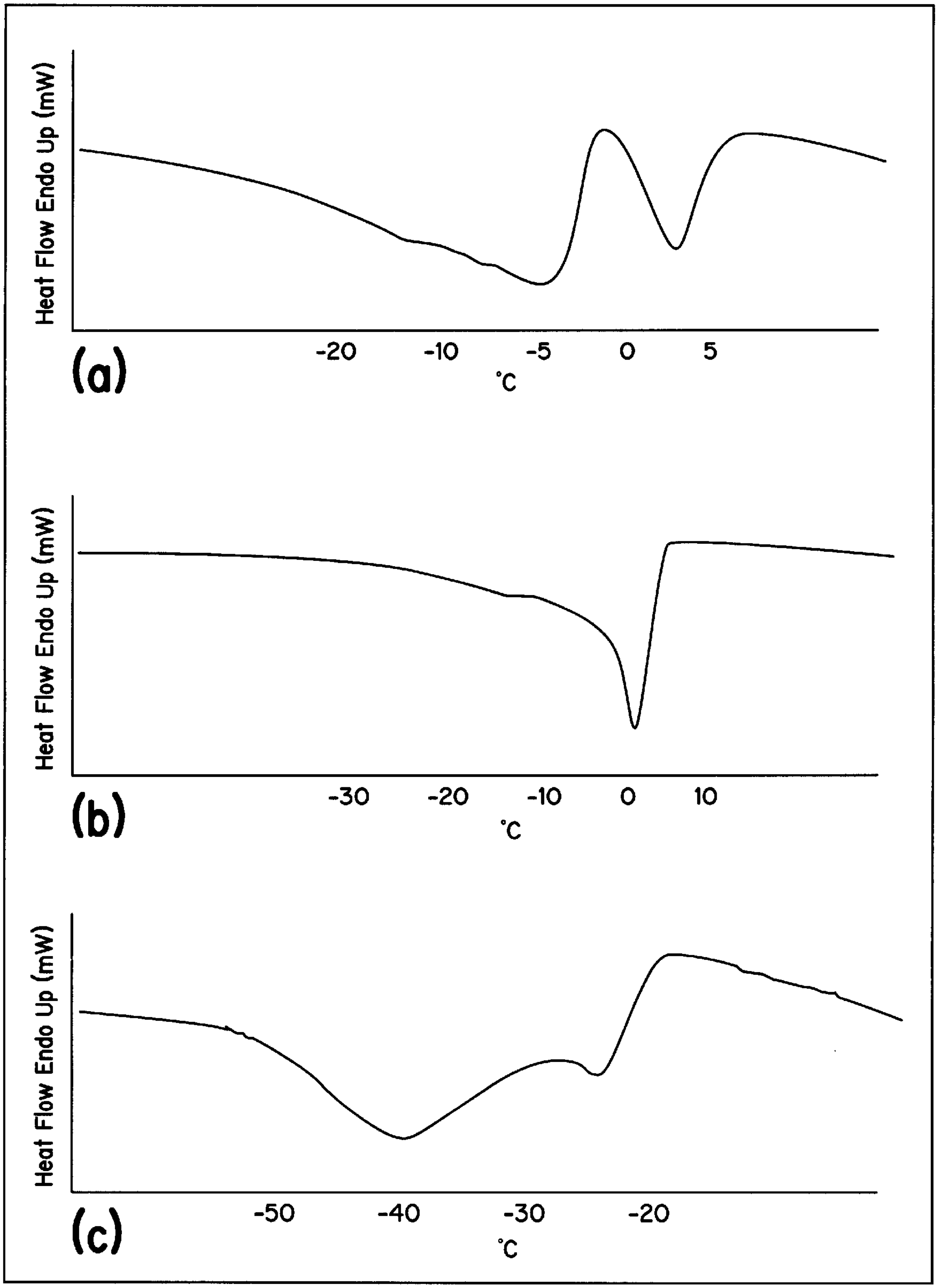

FIG. 5. DSC cooling curves (exotherm) for (a) partially hydrogenated menhaden oil (PHMO), (b) solid fraction, and (c) liquid fraction obtained from PHMO by acetone fractionation at −38° C.

DETAILED DESCRIPTION

With reference to FIGS. 1–5 and the following detailed description, MO and PHMO were dry fractionated and solvent fractionated as referred to above.

Materials

Menhaden oil (MO) and 14% boron trifloride ($BF_3$) in methanol were obtained from Sigma Chemical Company (St. Louis, Mo.) and partially hydrogenated menhaden oil (PHMO) was obtained from Omega Protein (Reedville, Va.). The iodine values for MO and PHMO were 164 and 118, respectively, as a measure of the unsaturation or number of double bonds in the oil. Acetone, analytical grade, was obtained from Baxter Health Corp. (Muskegon, Mich.). While acetone is employed in accordance with the preferred best current mode of the invention, in its broader aspects, other solvents may be employed for the fractionation such as acetone, isopropanol, hexane, ethanol, isooctane, and other $C_{1-18}$ alcohols, preferably ethanol and isopropanol.

Fatty Acid Methyl Ester (FAME) Analysis

Triacylglycerol (TAG) samples (20 mg) were reacted with 2 ml of 14% $BF_3$ in methanol at 80° C. for 15 min. After cooling on ice, 1 ml of saturated NaCl solution and 2 ml of isooctane were added and the mixture vortexed. The isooctane layer containing the FAME was dried with anhydrous sodium sulfate and analyzed by gas chromatograph (GC). A Hewlett-Packard (Alginent, Wilmington, Del.) Model 5890 Series II GC equipped with an automatic split injector and flame ionization detector was used for FAME analysis. The methyl esters were separated on a cross-linked polyethylene glycol column (HP-INNOWAX, 30 m×0.53 mm i.d., 0.25 μm film thickness). Helium was the carrier gas at a flow of 5.5 ml/min. The initial column temperature was 120° C., hold for 2 min, heated to 230° C. at 5° C./min, and hold at final temperature for 22 min. The injector and detector temperatures were 260° C.

Reverse-phase HPLC Analysis

TAG fractions were analyzed by non-aqueous reverse-phase HPLC on a Hewlett-Packard Model 1050 HPLC equipped with a Beckman/Altex Ultrasphere ODS 5 μm(4.6 mm×25 cm) column and a Varex (Burtonville, Md.) ELSD If mass detector. Estimation of partition numbers (PN) for individual TAG peaks in the fractions were made by comparison with a regression model constructed for PN versus retention times for a standard TAG mix (G-1) obtained from Nu-Chek-Prep (T. A. Foglia, et al., Enzymatic Interesterification of Tallow-Sunflower Oil Mixture, *J. Am. Oil Chem. Soc.,* 70, 1993, pp. 281–285). Solvent gradients and other HPLC conditions used were as described (Ibid.). The chromatograms of selected samples were divided into 4 retention time segments based on PN and the eluant for each segment isolated manually from the column for subsequent FAME analysis by insertion of a proportioning valve between the HPLC column and the detector.

Fourier Transform Infrared Spectroscopy (FTIR)

A Nicolet Impact 400D (Nicolet Instrument Inc., Madison, Wis.) FTIR spectrometer with Omnic operating software was used to measure trans-fatty acid content of the TAG fractions. The instrument was purged with nitrogen (0.4 psi) and sodium chloride cells (25 mm i.d.×4 mm thickness) were used for analysis. All spectra were recorded after 25 scans at a resolution of 1 $cm^{-1}$. For calibration, a reference background spectrum was taken for the clean empty cell, which was subtracted automatically from each recorded sample spectrum. Standard mixtures of methyl elaidate (5–60 wt %) in methyl oleate were prepared for construction of a trans-fatty acid standard curve. For trans acid analysis, each standard mix (about 30 mg) was dissolved in chloroform (1.2 ml and approximately 40 μm of the solution was applied onto the IR cells and solvent was evaporated with nitrogen for 5 min. TAG fractions, after conversion to FAME and after removal of solvent, were analyzed similarly for their trans-fatty acid content (*Official Methods and Recommended Practices of the American Oil Chemists' Society,* $5^{th}$ Edn., American Oil Chemists' Society, Champaign, 1998, Method Cd 14–95).

Differential Scanning Calorimetry (DSC)

Melting profiles for MO, PHMO and their fractions were obtained by DSC on a Perkin-Elmer (Perkin-Elmer Corp., Norwalk, Conn.) Model Pyris 1. Samples were heated to 80° C. and after 10 min at this temperature the cooling curve was obtained by cooling at 10° C./min until reaching −60° C. (Ibid., 1998, Method Cj 1–94).

Dry Fractionation

Approximately 5 g of MO or PHMO was placed into a 50 ml polypropylene centrifuge tube and fractionally crystallized at various temperatures for 24 h. After centrifugation (7600×g, 10 min) in a centrifuge adjusted to the fractionation temperature, the liquid phase was decanted from the solid phase. Before fractionation, MO and PHMO were held at 60° C. for 5 min and at 80° C. for 10 min, respectively, to remove memory effects of polymorphic TAG forms that may have been present originally.

Solvent Fractionation

Approximately 2 g of MO or PHMO was placed into a 50 ml polypropylene centrifuge tube and fractionally crystallized from acetone. The solute to solvent ratio used was 1:20 (w/v) and crystallization was conducted at three temperatures (−38° C., −18° C., and 0° C.). Other solute to solvent ratios (1:5 and 1:10) and temperatures (−10° C. and 5° C.) were studied but the results were not significantly different from those listed in Table 1. All solvent crystallization experiments were held at the specified temperature for 24 hours. After crystallization was completed, each centrifuge tube was placed into an insulated 250-ml wide mouth centrifuge bottle to minimize temperature changes during centrifugation. Decanting the liquid phase from the crystal pellet after centrifugation in a prechilled centrifuge (2100×g, 10 min) separated the liquid and solid phases. Acetone was removed from the fractions by evaporation under a stream of nitrogen at 60° C. until a constant fraction weight was obtained.

Statistics

The statistical comparisons were made according to Statistical Analysis System (SAS, Cary, N.C.) (1996). Bonferroni (Dunn) t test was performed on the means of values for fatty acid groupings. The tested significance level was p<0.05 (*SAS User's Guide, Release* 6.12 version, SAS Institute Inc., Cary, 1996).

Results and Discussion

The summed (Σ) wt % fatty acid class profile (Σ SFA, Σ MUFA, Σ PUFA, and Σ EPA+DHA) for MO (Table 1, entry 1) and PHMO (Table 1, entry 12) are listed in Table 1. Similarly listed are the fatty acid class profiles for the solid and liquid fractions obtained by dry fractionation of MO at −10° C., −5° C., and 0° C. (Table 1, entries 2–7) and PHMO at 18° C. and 30° C. (Table 1, entries 13–16). Dry fractionation of MO did not give an isolatable (<2%) solid fraction above 0° C. or a liquid fraction below −10° C. Similarly, PHMO remained mostly liquid above 31° C. and solid below 18° C. Dry fractionation of PHMO also was studied between 18° C. and 30° C. at 3° C. intervals (data not shown). In general, however, changes in the Σ SFA, Σ MUFA, Σ PUFA, and Σ EPA+DHA classes for the liquid and solid fractions produced were not significantly (p<0.05) different from those of the starting MO or PHMO. Both MO and PHMO are complex mixtures of TAG species that contain numerous fatty acids of varying carbon chain-length and degrees of unsaturation. Because of their complex nature, the crystallization of individual TAG species from MO and PHMO occurs over a wide temperature range, making it difficult to concentrate the TAG classes present in these oils by this process.

In general the separation of higher melting TAG from complex mixtures of TAG is facilitated when low-temperature solvent fractionation is used. This is so because TAG molecules generally form more stable crystals within shorter time periods when they are fractionally crystallized from a solvent. Although the use of a solvent adds additional costs to the fractionation process, solvent-fractionation has been used to prepare specialty fats (M. Bockisch, in *Fats and Oils Handbook,* AOCS Press, Champaign, Ill. 1998). Among solvents, acetone is considered as one of the more suitable for promoting stable TAG crystal formation (J. B. Rossell, Fractionation of Lauric Oils, *J. Am. Oil Chem. Soc.,* 62, 1985, pp. 385–390). Currently, the maximum permissible residue level for acetone is 30 ppm, (Code of Federal Regulations 21CFR 173.210). Accordingly, in this study, MO was solvent-fractionated from acetone at low-temperature (−38° C., −18° C., and 0° C.). For the −38° C. liquid fraction, the Σ EPA+DHA content increased (p<0.05) to 35.3% compared to the 30.4% in neat MO, and the yield recovery of the fraction was 62 wt % (Table 1, entry 8). For the −18° C. and 0° C. liquid fractions, the Σ EPA+DHA content in these fractions was similar to that of MO. On the other hand, the Σ MUFA and Σ PUFA in the liquid fraction at −38° C. and the Σ MUFA, Σ PUFA, and Σ EPA+DHA in the liquid fraction at −18° C. and −0° C. were not significantly different from that of MO. However, the −38 C and −18° C. solid fractions (Table 1, entries 9 and 11) had significant increases in Σ SFA, but their wt % recovery was small especially for the −18° C. solid fraction. Apparently, the solvent fractionation temperatures and solvent ratio used in this study did not allow for the selective fractionate of the MUFA, PUFA containing TAG from MO.

Acetone fractionation of PHMO resulted in a significant increase in the Σ MUFA in the liquid fractions obtained at the three temperatures studied (Table 1, entries 17, 19, and 21). Compared to neat PHMO, the Σ MUFA in the liquid fractions increased with decreasing fractionation temperature by 10% to 24% and the wt % recovery of the fractions ranged from 34% to 68%. Surprisingly, when the fractionation temperature was decreased from 0° C. to −38° C., the Σ MUFA in liquid fraction increased by 12% even though the wt % recovery decreased by half. As expected, as the Σ MUFA increased significantly the Σ SFA decreased significantly in the liquid fractions from PHMO. Conversely, for the solid fractions significant increases in Σ SFA were accompanied by significant decreases in the Σ MUFA (Table 1, entries 18, 20, and 22).

The hardening of oils by hydrogenation of the unsaturated fatty acids in fats and oils has been an important industry practice since the early 1900's (M. Bockisch, in *Fats and Oils Handbook,* AOCS Press, Champaign, Ill. 1998). Hydrogenation, however, also induces isomerization of the cis unsaturated fatty acids to trans isomers, which are not commonly present in natural fats and oils. In general, it is suggested that the dietary intake of trans-fatty acids should be limited (E. A. Emken, Do trans Acids Have Adverse Health Consequences?, in *Health Effects of Dietary Fatty Acids,* edited by G. J. Nelson, AOCS Press, Champaign, Ill. 1991, pp. 245–263). Accordingly, to answer the question as to whether dry or solvent fractionation processes could produce fractions of lower trans-fatty acid content from PHMO, we measured the percent trans-fatty acid content for PHMO and the various fractions obtained from it (Table 1). For neat PHMO, a 33.1% trans-fatty acid content was determined (Table 1, entry 12). In the solid and liquid fractions, the trans-fatty acid content ranged between 30.3% to 36.0%, values not statistically different from PHMO itself, which indicated that the trans fatty acid-containing TAG were not fractionated from cis fatty acid-containing TAG by the processes used in this study.

Figure 1:
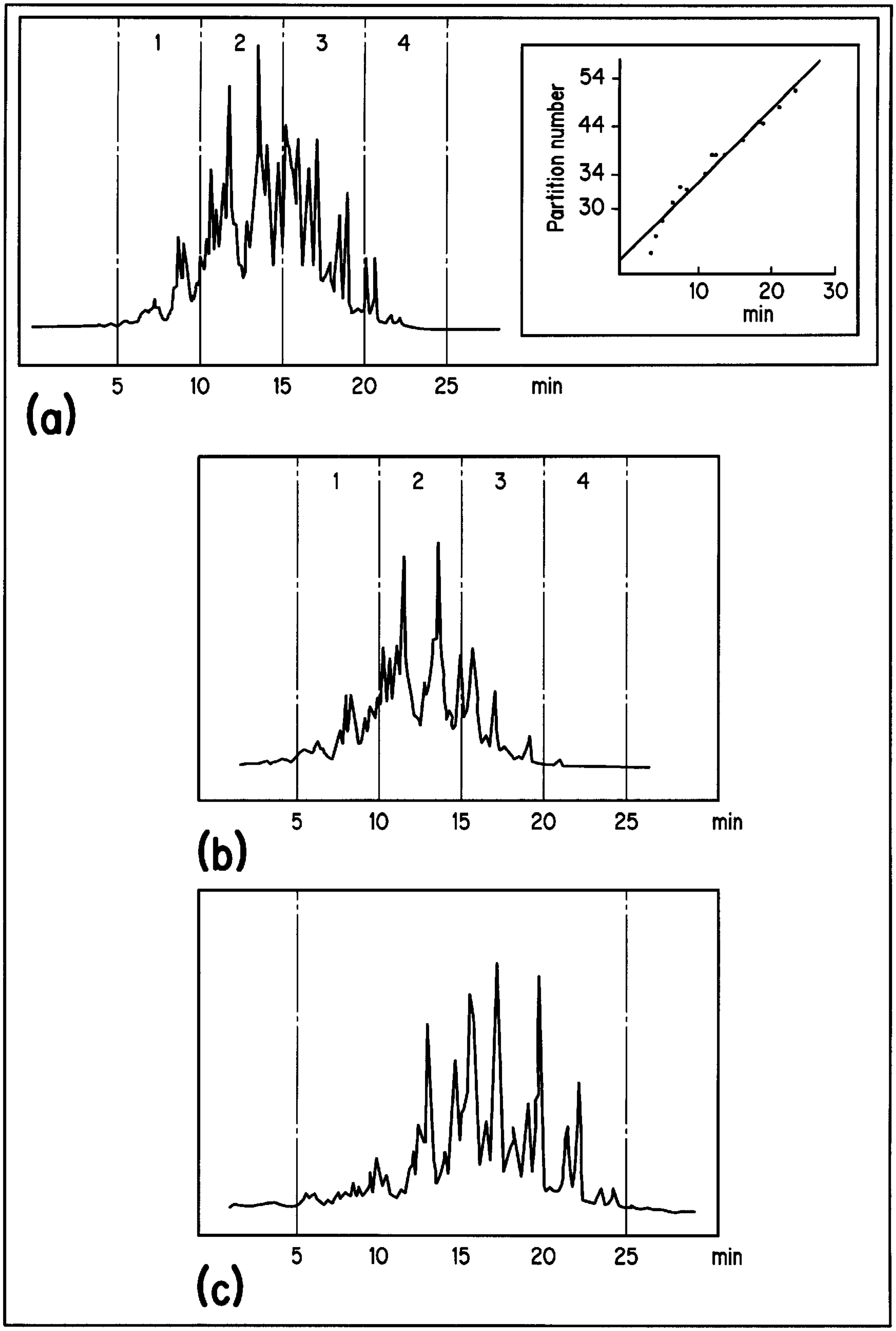
FIG. 1. Reverse-phase high performance liquid chromatography (HPLC) chromatograms for (a) menhaden oil (MO), (b) liquid, and (c) solid fractions obtained from MO at −38° C. Chromatograms (a) and (b) are divided into 4 segments based on partition number. Insert: Regression plot of triacylglycerol partition number (PN) versus retention time for standard triacylglycerol mixture.

MO, PHMO, and the liquid and solid fractions obtained from them by solvent fractionation at −38° C. were analyzed by non-aqueous reverse phase HPLC. The HPLC separations obtained are presented in FIGS. 1 and 2. Reverse-phase HPLC, which separates TAG molecular species according to carbon chain-length and number of double bonds of the acyl moieties that constitute the TAG, is widely used in the analysis of fats and oils (Christie, *HPLC and Lipids,* Pergamon Press, New York, 1987, pp. 42–102). The HPLC chromatogram for MO (FIG. 1*a*) showed a poor resolution of TAG molecular species because MO is a complex mixture of TAG composed of fatty acids with carbon chains from C14 to C24, which may contain from zero to six double bonds. The chromatogram, however, could be segmented into regions of TAG partition numbers (PN) based on the retention times of TAG standards. Accordingly, the HPLC chromatograms of MO and its −38° C. liquid and solid fractions were divided into four retention time segments (FIG. 1). Each segment corresponded to TAG having the following range of PN's: segment 1 (PN: 32–38); segment 2 (PN: 38–42); segment 3 (PN: 42–48); and segment 4 (PN: >48). In the HPLC chromatogram of MO, TAG with PN 38–42 and PN 42–48 (FIG. 1*a,* segments 2 and 3) accounted for 43% and 41% of the TAG in MO while only 7% of the TAG had PN>48. TAG in the −38° C. liquid fraction from MO (FIG. 1*b*) showed a similar distribution of TAG until PN 42 (FIG. 1*b,* segment 2), thereafter several TAG peaks, assumed to be TAG containing more saturated fatty acids, were reduced or eliminated. About 36% of the TAG in this fraction had PN>42 whereas for MO they accounted for 48% of the TAG. In contrast, the chromatogram of the −38° C. solid fraction (FIG. 1*c*) indicated that about 77% of the TAG in the solid fraction had PN>42.

The HPLC segments for MO and its −38° C. liquid fraction were isolated and analyzed by GC to determine their fatty acid composition (Table 2). The tabulated data (Table 2) are intended for qualitative comparison only. The individual fatty acid composition and summed (Σ) fatty acid classes for the MO-TAG in segment 1 ($MO_1$) were 28.4%Σ SFA, 17.9% Σ MUFA, 17.6%Σ PUFA, and 36.1% Σ EPA+DHA. This suggested that most TAG species in this segment might contain one EPA or DHA moiety. In segment 4 ($MO_4$), the fatty acid class distribution was 41% Σ SFA, 27% Σ MUFA, 26% Σ PUFA, and 6% Σ EPA+DHA, which suggests that EPA or DHA acyl residues are not present in most TAG species. On the other hand, segment 4 ($MOL_4$) of the −38° C. liquid fraction from MO was composed of 30% Σ SFA, and 42% Σ MUFA, and 28% Σ PUFA, suggesting that TAG species in this segment for the most part are composed of one saturated and two unsaturated (MUFA or PUFA) acyl residues. From Table 2, we concluded that Σ MUFA content was significantly enriched in TAG molecules with PN 32–38 ($MOL_1$) and in TAG molecules with PN>48 ($MOL_4$) of the −38° C. liquid fraction from MO.

Figure 2:
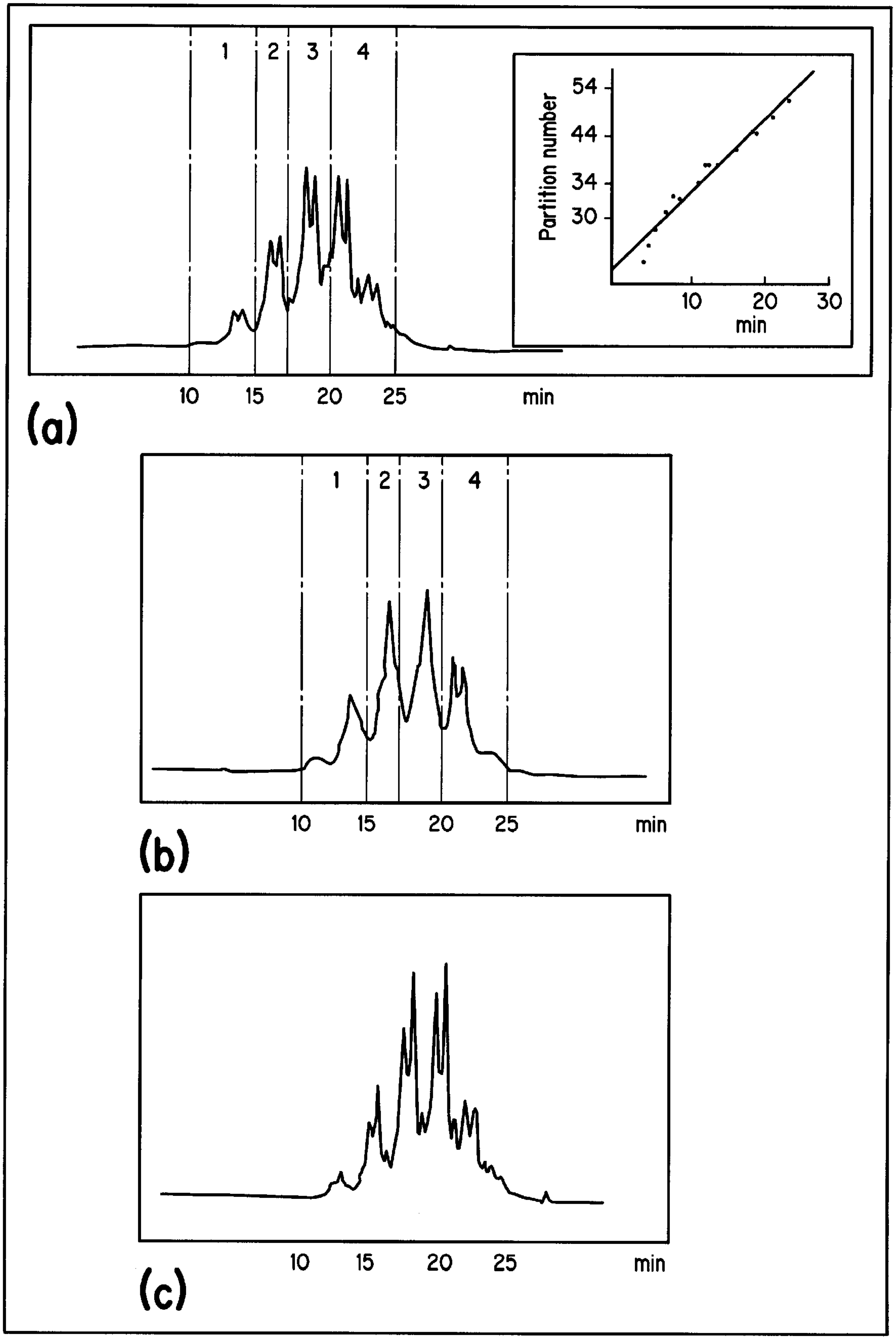
FIG. 2. Reverse-phase HPLC chromatograms for (a) partially hydrogenated menhaden oil (PHMO), (b) liquid, and (c) solid fractions obtained from PHMO by acetone crystallization at −38° C. Chromatograms (a) and (b) are divided into 4 segments based on partition number. Insert.

Similarly, FIG. 2 shows the HPLC chromatogram for PHMO and the −38° C. liquid and solid fractions obtained from it. As for MO, the chromatograms were divided into 4 retention time segments identified as $PHMO_1$ and PHMOL, (PN: ≦42); $PHMO_2$ and $PHMOL_2$ (PN: 44–46); $PHOM_3$ and $PHMOL_3$ (PN: 48–50) and $PHMO_4$ and $PHMOL_4$ (PN>50), respectively. For PHMO (FIG. 2*a*), TAG species with PN: ≧48 account for about 77% of the TAG and only 3.8% of TAG species have PN ≦42. For the −38° C. liquid fraction from PHMO (FIG. 2*b*), however, TAG species with PN ≧48 accounted for about 54% of TAG and TAG species with PN ≦42 increased to 14% of TAG. In the −38° C. solid fraction (FIG. 2*c*) the bulk of the TAG in this fraction eluted in segment 4 (PN: >50). For the PHMO-TAG segments (Table 3), the MUFA content ranged from 27% ($PHMO_3$) tp 43% ($PHMO_2$). However, the MUFA content for the HPLC segments of the −38° C. liquid fraction from PHMO varied from 42% ($PHMOL_1$) to 59% ($PHMOL_{3\&4}$) (Table 3). The foregoing indicated that in addition to carbon chain length the degree of unsaturation also effected the fractionation of TAG present in the PHMO.

The percent solid fat content (SFC) curves for MO and PHMO and the solid and liquid fractions obtained from them by acetone fractionation at −38° C. are shown in FIG. 3. MO and its −38° C. solid fraction have 50% SFC at −11.4° C. and −7.5° C., respectively, while the −38° C. MO liquid fraction has 50% SFC at −46.5° C. (FIG. 3*a*). For PHMO and its −38° C. solid fraction the 50% SFC are at −10.3° C. and −1.5° C., respectively, while the corresponding liquid fraction has 50% SFC at −35.4° C. (FIG. 3*b*). As anticipated, the SFC data show that acetone fractionation of both MO and PHMO concentrated the higher and lower melting TAG molecular species in the oils into the solid and liquid fractions, respectively.

The DSC cooling curve for MO showed a crystallization onset temperature ($T_c$) (I. Lee, et al., Use of Branched-Chain Ester to Reduce the Crystallization Temperature of Biodiesel, *J. Am. Oil Chem. Soc.,* 72, 1995, pp. 1115–1160) at 3.2° C. and a broad low-temperature $T_c$ at −4.3° C. (FIG. 4*a*). In contrast, for the −38° C. MO solid fraction the DSC cooling curve (FIG. 4*b*) showed only one exotherm peak with a sharp $T_c$ at 1.5° C., which, like the SFC observation, suggested that the higher melting TAG species present in MO were preferentially concentrated (co-crystallized) into this fraction. The DSC cooling curve for the −38° C. MO liquid fraction had two exothermic peaks at approximately −24° C. and −40° C., which did not, however, have distinctly defined $T_c$'s (FIG. 4*c*). The DSC crystallization curve for PHMO also showed two distinct exotherm peaks, one with a $T_c$ of 9.8° C. and a lower-temperature exotherm with $T_c$ at −3.4° C. (FIG. 5*a*). Similarly, the cooling curve for the −38° C. PHMO solid fraction had a sharp exotherm peak with $T_c$ at 13.7° C. and a lower-temperature exotherm with $T_c$ at 0.2° C. (FIG. 5*b*), which suggested that co-crystallization of high-melting TAG species had not occurred. On the other hand, the cooling curve for the −38° C. PHMO liquid fraction showed a $T_c$ of −22° C., and a broad indistinct exotherm around −22° C. (FIG. 5*c*).

The foregoing demonstrates that under the appropriate conditions it is possible to dry fractionate and/or solvent-fractionate menhaden oil and/or partially hydrogenated menhaden oil into various solid and liquid fractions that are enriched in either saturated, monounsaturated, polyunsaturated, or the n-3 classes of fatty acids. Moreover, characterization of these TAG fractions by reverse-phase HPLC gives insight into the compositional nature of the TAG that are concentrated into the various fractions produced by these fractionation processes. Finally, the DSC crystallization patterns for the fractions in conjunction with their fatty acid compositional data should allow for the optimization of the fractionation schemes developed in this study. This information should allow for the production of specific TAG fractions from MO and PHMO that are potentially useful as functional lipid products.

TABLE 1

Summed (Σ) Distribution of Fatty Acid Classes for Fractions Produced by Either Dry or Wet (solvent:acetone) Fractionation of Mo and PHMO[a]

| Entry | | Σ SFA | Σ MUFA | Σ PUFA | Σ EPA & DHA | % trans | Wt % |
|---|---|---|---|---|---|---|---|
| 1 | MO | $35.1^{h}$ | $24.3^{g}$ | $10.2^{ef}$ | $30.4^{fg}$ | — | — |
| 2 | MO-10L[b] | $32.3^{hi}$ | $25.4^{efg}$ | $13.0^{e}$ | $29.3^{ef}$ | — | 10.8 |
| 3 | MO-10S[b] | $37.4^{g}$ | $24.4^{efg}$ | $10.4^{fg}$ | $27.8^{fg}$ | | 89.2 |
| 4 | MO-5L[b] | $31.9^{i}$ | $24.5^{efg}$ | $11.3^{e}$ | $32.3^{ef}$ | — | 53.7 |
| 5 | MO-5S[b] | $39.0^{g}$ | $22.1^{fgh}$ | $10.2^{ef}$ | $28.7^{fg}$ | — | 46.3 |
| 6 | MO-0L[b] | $34.0^{hi}$ | $23.9^{efg}$ | $10.9^{ef}$ | $31.2^{efg}$ | — | 67.0 |
| 7 | MO-0S[b] | $38.6^{g}$ | $22.1^{fgh}$ | $10.6^{ef}$ | $28.7^{fg}$ | — | 33.0 |
| 8 | MO-38L[c] | $27.3^{j}$ | $26.3^{e}$ | $11.1^{ef}$ | $35.3^{e}$ | — | 62.2 |
| 9 | MO-38S[c] | $46.4^{f}$ | $21.3^{gh}$ | $8.7^{f}$ | $23.6^{h}$ | — | 37.8 |
| 10 | MO-18L[c] | $32.5^{hi}$ | $24.4^{ef}$ | $11.2^{ef}$ | $31.9^{ef}$ | — | 86.3 |
| 11 | MO-18S[c] | $55.3^{e}$ | $18.9^{h}$ | $7.4^{f}$ | $18.4^{h}$ | — | 13.7 |
| 12 | PHMO | $49.7^{g}$ | $47.1^{hi}$ | $3.2^{ef}$ | — | $33.1^{ef}$ | — |
| 13 | PHMO-30L[b] | $49.1^{g}$ | $46.0^{hi}$ | $4.8^{e}$ | — | $31.8^{ef}$ | 89.2 |
| 14 | PHMO-30S[b] | $53.4^{ef}$ | $43.0^{ij}$ | $3.6^{ef}$ | — | $32.0^{ef}$ | 10.8 |
| 15 | PHMO-18L[b] | $46.6^{g}$ | $49.8^{gh}$ | $3.6^{ef}$ | — | $30.5^{f}$ | 22.7 |
| 16 | PHMO-18S[b] | $52.1^{fg}$ | $45.0^{hi}$ | $2.9^{f}$ | — | $33.7^{ef}$ | 77.3 |
| 17 | PHMO-38L[c] | $34.5^{i}$ | $58.4^{e}$ | $3.3^{ef}$ | — | $31.2^{ef}$ | 33.8 |
| 18 | PHMO-38S[c] | $54.2^{ef}$ | $43.1^{ij}$ | $2.7^{f}$ | — | $33.3^{ef}$ | 66.2 |
| 19 | PHMO-18L[c] | $40.5^{h}$ | $55.1^{ef}$ | $4.5^{e}$ | — | $35.8^{e}$ | 49.5 |
| 20 | PHMO-18S[c] | $57.3^{e}$ | $39.9^{f}$ | $2.8^{f}$ | — | $36.0^{e}$ | 50.5 |
| 21 | PHMO-0L[c] | $40.8^{h}$ | $51.6^{fg}$ | $3.5^{ef}$ | — | $3.49^{ef}$ | 67.5 |
| 22 | PHMO-0S[c] | $53.4^{fg}$ | $37.1^{f}$ | $2.4^{f}$ | — | $34.9^{ef}$ | 32.5 |

[a]Fatty acid composition determined by GC (area %): SFA: saturated fatty acids; MUFA: monounsaturated fatty acids; PUFA: polyunsaturated fatty acids; EPA: eicosapentaenoic acid; and DHA: docosahexaenoic acid. Weight percent (wt %) recovery defined as sum of liquid and solid fractions, e.g., MO-5L + MO-5S = 100%

[b]Dry fractionation carried out at 0° C., −5° C. and −10° C. for MO and at 18° C. and 30° C. for PHMO.

[c]Solvent (acetone) fractionation of MO and PHMO carried out at 0° C., −18° C., and −38° C. No crystallization of MO occurred at temperatures ≧0° C.

[d]Mean values within a column having a similar superscript ([e–j]) do not differ significantly ($p < 0.05$). The analyses are for entries 1–11 and 12–22, respectively, for MO and PHMO.

TABLE 2

Fatty Acid Composition of Menhaden Oil (MO), −38° C. Liquid Fraction from Menhaden Oil (MOL), and Their Segmented Reverse-Phase LPLC Fractions[a,b]

| Fatty Acid | MO | $MO_1$ | $MO_2$ | $MO_3$ | $MO_4$ | MOL | $MOL_1$ | $MOL_2$ | $MOL_3$ | $MOL_4$ |
|---|---|---|---|---|---|---|---|---|---|---|
| C14:0 | 10.7$^{d}$ | 7.4$^{c}$ | 9.8$^{de}$ | 11.4$^{d}$ | 6.6$^{f}$ | 9.2$^{d}$ | 4.4$^{f}$ | 7.7$^{de}$ | 6.9$^{e}$ | 2.8$^{f}$ |
| C14:1 | 0.4$^{e}$ | 0.8$^{e}$ | 0.4$^{e}$ | 0.3$^{e}$ | 0.7$^{d}$ | 0.7$^{d}$ | 0.4$^{e}$ | 0.8$^{d}$ | 0.6d$^{e}$ | — |
| C16:0 | 20.6$^{e}$ | 7.6$^{g}$ | 14.4$^{f}$ | 26.7$^{d}$ | 25.0$^{d}$ | 15.5$^{e}$ | 18.4$^{d}$ | 15.9$^{e}$ | 18.7$^{d}$ | 15.8$^{e}$ |
| C16:1 | 14.1$^{d}$ | 10.3$^{3}$ | 11.6$^{e}$ | 14.9$^{d}$ | 10.0$^{e}$ | 16.4$^{d}$ | 5.7$^{f}$ | 10.9$^{e}$ | 16.4$^{d}$ | 8.6$^{e}$ |
| C18:0 | 3.8$^{g}$ | 13.4$^{d}$ | 3.6$^{g}$ | 5.3$^{f}$ | 9.3$^{e}$ | 2.6$^{g}$ | 17.5$^{d}$ | 5.8$^{f}$ | 3.9$^{fg}$ | 11.1$^{e}$ |
| C18:1 | 9.8$^{e}$ | 6.8$^{f}$ | 8.3$^{e}$ | 11.1$^{e}$ | 15.9$^{d}$ | 9.2$^{g}$ | 27.3$^{e}$ | 7.2$^{g}$ | 11.1$^{f}$ | 33.1$^{d}$ |
| C18:2 | 2.2$^{g}$ | 10.4$^{e}$ | 6.6$^{f}$ | 4.1$^{g}$ | 14.4$^{d}$ | 1.9$^{g}$ | 10.0$^{e}$ | 10.8$^{e}$ | 8.7$^{f}$ | 21.0$^{d}$ |
| C18:3 | 2.5$^{f}$ | 7.2$^{e}$ | 6.5$^{e}$ | 2.5$^{f}$ | 12.0$^{d}$ | 1.3$^{f}$ | 6.1$^{e}$ | 8.2$^{d}$ | 5.5$^{e}$ | 7.4$^{de}$ |
| C20:4 | 2.0 | — | 1.3 | 1.2 | — | 3.7$^{d}$ | — | 1.2$^{e}$ | 1.5$^{e}$ | — |
| C20:5 | 19.2$^{ef}$ | 24.6$^{d}$ | 22.1$^{de}$ | 11.8$^{f}$ | 6.1$^{g}$ | 22.6$^{d}$ | 5.6$^{g}$ | 16.9$^{e}$ | 12.2$^{f}$ | — |
| C22:5 | 3.5 | — | 3.5 | 2.8 | — | 4.2$^{d}$ | — | 2.4$^{e}$ | 3.1$^{e}$ | — |
| C22:6 | 11.2$^{d}$ | 11.5$^{d}$ | 11.9$^{d}$ | 7.9$^{e}$ | — | 12.7$^{d}$ | 4.6$^{e}$ | 12.2$^{d}$ | 11.3$^{d}$ | — |
| Σ SFA$^{e}$ | 35.1$^{e}$ | 28.4$^{f}$ | 27.8$^{f}$ | 43.4$^{d}$ | 40.9$^{d}$ | 27.3$^{e}$ | 40.3$^{d}$ | 29.4$^{e}$ | 29.5$^{e}$ | 29.7$^{g}$ |
| Σ MUFA$^{c}$ | 24.3$^{d}$ | 17.9$^{f}$ | 20.3$^{e}$ | 26.3$^{d}$ | 26.6$^{d}$ | 26.3$^{f}$ | 33.4$^{g}$ | 18.9$^{g}$ | 28.1$^{f}$ | 41.7$^{d}$ |
| Σ PUFA$^{c}$ | 10.2 | 17.6$^{e}$ | 17.9$^{e}$ | 10.6$^{f}$ | 26.4$^{d}$ | 11.1$^{g}$ | 16.1$^{f}$ | 22.6$^{e}$ | 18.8$^{ef}$ | 28.4$^{d}$ |
| Σ EPA + DHA$^{c}$ | 30.4$^{e}$ | 36.1$^{d}$ | 34.0$^{de}$ | 19.7$^{f}$ | 6.1$^{g}$ | 35.3$^{3}$ | 10.2$^{f}$ | 29.1$^{de}$ | 23.5$^{e}$ | — |

[a]Liquid fraction obtained by crystallization from acetone at −38° C. Fatty acid composition determined by GC (area %): $MO_{1-4}$ and $MOL_{1-4}$ represent the isolated MO and MOL triacylglycerol segments shown in FIG. 1.
[b]Area percent fatty acid as determined by GC. Mean values for MO–$MO_4$ and MOL–$MOL_4$ within the same row having a similar superscript ($^{d-g}$) are not significantly different ($p < 0.05$).
[c]SFA: saturated fatty acids; MUFA: monounsaturated fatty acids; PUFA: polyunsaturated fatty acids; EPA: eicosapentaenoic acid; and DHA: docosahexaenoic acid.

TABLE 3

Fatty Acid Composition of Partially Hydrogenated Menhaden Oil (PHMO), −38° C. Liquid Fraction from Partially Hydrogenated Menhaden Oil (PHMOL), and Their Segmented Reverse-Phase HPLC Fractions[a,b]

| Fatty Acid | PHMO | $PHMO_1$ | $PHMO_2$ | $PHMO_3$ | $PHMO_4$ | PHMOL | $PHMOL_1$ | $PHMOL_2$ | $PHMOL_3$ | $PHMOL_4$ |
|---|---|---|---|---|---|---|---|---|---|---|
| C14:0 | 12.5$^{d}$ | 10.9$^{e}$ | 9.1$^{ef}$ | 6.3$^{f}$ | 5.9$^{f}$ | 11.3$^{d}$ | 11.5$^{d}$ | 9.0$^{e}$ | 5.5$^{f}$ | 4.2$^{f}$ |
| C16:0 | 29.1$^{de}$ | 32.2$^{d}$ | 29.3$^{de}$ | 25.2$^{e}$ | 35.8$^{d}$ | 20.7$^{e}$ | 15.4$^{f}$ | 23.0$^{de}$ | 25.9$^{d}$ | 22.1$^{de}$ |
| C16.1 | 21.3$^{d}$ | 13.4$^{e}$ | 13.8$^{e}$ | 7.5$^{f}$ | 7.6$^{f}$ | 29.0$^{d}$ | 25.9$^{de}$ | 21.2$^{e}$ | 10.5$^{f}$ | 8.5$^{e}$ |
| C18:0 | 5.1$^{f}$ | 17.3$^{e}$ | 14.0$^{e}$ | 38.6$^{d}$ | 13.4$^{e}$ | 3.1$^{g}$ | 30.9$^{d}$ | 7.0$^{fg}$ | 16.9$^{e}$ | 11.1$^{ef}$ |
| C18:1 | 21.7$^{e}$ | 23.4$^{e}$ | 23.9$^{e}$ | 13.3$^{f}$ | 27.8$^{d}$ | 26.4$^{e}$ | 16.3$^{f}$ | 32.4$^{d}$ | 33.0$^{d}$ | 37.1$^{d}$ |
| C20:0 | 0.6$^{f}$ | 2.8$^{e}$ | 4.6$^{d}$ | 1.5$^{ef}$ | 4.1$^{d}$ | 0.3$^{f}$ | — | 2.8$^{e}$ | 2.7$^{e}$ | 3.6$^{d}$ |
| C20:1 | 7.5$^{d}$ | — | 5.3$^{e}$ | 1.3$^{f}$ | 3.1$^{ef}$ | 6.4$^{e}$ | — | 4.1$^{f}$ | 5.1$^{ef}$ | 13.2$^{d}$ |
| C22:0 | 0.2$^{f}$ | — | — | 1.0$^{e}$ | 2.3$^{d}$ | 0.3 | — | — | — | 0.2 |
| C22:1 | 2.0 | — | — | 5.1 | — | 2.5$^{d}$ | — | 0.5$^{e}$ | 0.4$^{e}$ | — |
| Σ SFA$^{c}$ | 47.5$^{f}$ | 63.2$^{e}$ | 57.0$^{ef}$ | 72.6$^{d}$ | 61.5$^{e}$ | 35.7$^{f}$ | 57.8$^{d}$ | 41.8$^{e}$ | 51.0$^{de}$ | 41.2$^{e}$ |
| Σ MUFA$^{c}$ | 52.5$^{d}$ | 36.8$^{f}$ | 43.0$^{e}$ | 27.2$^{f}$ | 38.5$^{f}$ | 64.3$^{d}$ | 42.2$^{f}$ | 58.2$^{d}$ | 49.0$^{e}$ | 58.8$^{d}$ |

[a]Liquid fraction obtained by crystallization from acetone at −38° C. $PHMO_{1-4}$ and $PHMOL_{1-4}$ values represent the isolated PHMO and PHMOL triacylglycerol HPLC segments shown in FIG. 2.
[b]Area percent fatty acid as determined by GC. Mean values for PHMO–$PHMO_4$ and PHMOL–$PHMOL_4$ within the same row having a similar superscript ($^{d-g}$) are not significantly different ($p < 0.05$).
[c]SFA: saturated fatty acids; MUFA: monounsaturated fatty acids.

In view of the above detailed description, it will become apparent to those of ordinary skill in the art that other variations of the method and compositions may be made without departing from the spirit and scope of this invention.

What is claimed is:

1. A method of making a lipid composition enriched in unsaturated fatty acid esters from menhaden oil comprising providing an oil selected from the group consisting of menhaden oil (MO) and partially hydrogenated menhaden oil (PHMO) having original amounts of unsaturated fatty acid esters and saturated fatty acid esters, mixing said oil with solvent to fractionate said oil, maintaining said mixture at a temperature and for a sufficient time to facilitate said solvent fractionation of a lipid composition having an increased amount of said unsaturated fatty acid esters and a decreased amount of said saturated fatty acid esters relative to said original amounts, and isolating the lipid composition enriched in said unsaturated fatty acid esters.

2. The method of claim 1 comprising the further step of separating said oil into a solid phase and liquid phase by dry fractionation prior to mixing the liquid phase with solvent for said fractionation.

3. The method of claim 2 wherein the oil is liquified prior to said dry fractionation at a temperature range of about −10° C. to about 35° C.

4. The method of claim 1 wherein the solvent is selected from the group consisting of acetone, isopropanol, hexane, ethanol, isooctane and $C_1$–$C_{18}$ alcohols.

5. The method of claim 1 wherein the solvent is acetone.

6. The method of claim 1 wherein said solvent fractionation is conducted at a temperature below the range of about 0° C. to about −15° C.

7. The method of claim 1 wherein said solvent fractionation is conducted at a temperature range of about 0° C. to about −40° C.

8. The method of claim 1 wherein said solvent fractionation produces a liquid fraction and a solid fraction followed by separating the liquid fraction containing the lipid composition from the solid fraction by centrifugation, cold pressing or vacuum filtration.

9. The method of claim 8 comprising the further step of removing solvent from said lipid composition to a level fit for human consumption.

10. The method of claim 8 wherein the liquid fraction is separated from the solid fraction by centrifugation at a temperature below the range of about 0° C. to about −15° C.

11. The method of claim 8 wherein said liquid fraction is separated from the solid fraction by centrifugation at a temperature range of about 0° C. to about −40° C.

12. The method of claim 1 wherein said unsaturated fatty acid esters are selected from the group consisting of C14:1, C16:1, C18:1, C18:2, C18:3, C20:4, C20:5, C22:5 and C22:6, and mixtures thereof.

13. The method of claim 12 wherein the monounsaturated fatty esters consist mainly of C16:1 and C18:1.

14. The method of claim 1 wherein said lipid composition has an amount of unsaturated fatty acid esters which is increased about 5% to about 32% by weight and an amount of saturated fatty acid esters which is decreased about 7% to about 31% by weight, both amounts relative to their original amounts in the oil.

15. The method of claim 1 wherein said solvent fractionation produces a liquid fraction and a solid fraction followed by separating the liquid fraction containing the liquid composition from the solid fraction and wherein the liquid fraction has an amount of unsaturated fatty esters which is increased about 18% to about 32% by weight and an amount of saturated fatty acid esters which is decreased about 7% to about 31% by weight, both amounts relative to their original amounts in the oil.

16. The method of claim 1 wherein said unsaturated fatty acid esters contain monounsaturated fatty acid esters in an amount from about 0.5% to about 24% by weight relative to original amounts of monounsaturated fatty acid esters in the oil.

17. The method of claim 1 wherein said lipid composition has an amount of polyunsaturated fatty esters which is increased about 3% to about 40% by weight and an amount of saturated fatty acid esters which is decreased about 5% to about 50% by weight, both amounts relative to their original amounts in the oil.

18. The method of claim 1 wherein said lipid composition has an amount of 5,8,11,14,17-eicosapentaenoic acid ester (EPA) and 4,7,10,13,18,19-docosahexaenoic acid ester (DHA) which is increased from about 5% to about 18% by weight relative to the original amounts of said EPA and DHA acid esters in the oil.

19. A method of making a lipid composition enriched in unsaturated fatty acid esters from oil comprising providing oil selected from the group consisting of menhaden oil (MO) and partially hydrogenated menhaden oil (PHMO) having original amounts of unsaturated fatty acid esters and saturated fatty acid esters, mixing said oil with acetone to fractionate said oil, maintaining said mixture at a temperature of about ambient temperature to about −40° C. for a sufficient time to facilitate said solvent fractionation of a lipid composition having an increased amount of said unsaturated fatty acid esters and a decreased amount of said saturated fatty acid esters relative to said original amounts, separating a liquid fraction containing the lipid composition from a solid fraction, and isolating the lipid composition enriched in said unsaturated fatty acid esters from the liquid fraction.

20. The method of claim 19 wherein the solvent fractionation is conducted at a temperature of about 0° C. to about −38° C.

21. The method of claim 19 wherein said solvent fractionation is conducted at a temperature of about −38° C.

22. The method of claim 19 comprising the further step of separating said oil into a solid phase and a liquid phase prior to mixing the liquid phase with solvent for said fractionation.

23. The method of claim 22 wherein the oil is liquified prior to said separation.

24. The method of claim 19 wherein said solvent fractionation is conducted at a temperature of about 10° C. to about −40° C.

25. The method of claim 19 wherein said solvent fractionation produces a liquid fraction and a solid fraction followed by separating the liquid fraction containing the lipid composition from the solid fraction by centrifugation, cold pressing or vacuum filtration.

26. The method of claim 25 comprising the further step of removing acetone from said lipid composition to a level fit for human consumption.

27. The method of claim 19 wherein said unsaturated fatty acid esters are selected from the group consisting of C14:1, C16:1, C18:1, C18:2, C18:3, C20:4, C20:5, C22:5 and C22:6, and mixtures thereof.

28. The method of claim 19 wherein the monounsaturated fatty esters consist mainly of C16:1 and C18:1.

29. The method of claim 19 wherein said lipid composition has an amount of unsaturated fatty acid esters which is increased about 5% to about 32% by weight and an amount of saturated fatty acid esters which is decreased about 7% to about 31% by weight, both amounts relative to their original amounts in the oil.

30. The method of claim 19 wherein said solvent fractionation produces a liquid fraction and a solid fraction followed by separating the liquid fraction containing the liquid composition from the solid fraction and wherein the liquid fraction has an amount of unsaturated fatty esters which is increased about 18% to about 32% by weight, and an amount of saturated fatty acid esters which is decreased about 7% to about 31% by weight, both amounts relative to their original amounts.

31. The method of claim 19 wherein said unsaturated fatty acid esters contain monounsaturated fatty acid esters in an amount from about 0.5% to about 24% by weight relative to original amounts of monounsaturated fatty acid esters in the oil.

32. The method of claim 19 wherein said lipid composition has an amount of polyunsaturated fatty esters which is increased about 3% to about 40% by weight and an amount of saturated fatty acid esters which is decreased about 5% to about 50% by weight, both amounts relative to their original amounts in the oil.

33. The method of claim 19 wherein said lipid composition has an amount of 5,8,11,14,17-eicosapentanoic acid ester (EPA) and 4,7,10,13,16,19-docosahexaenoic acid ester (DHA) which is increased from about 5% to about 18% by weight relative to the original amounts of said EPA and DHA acid esters in the oil.

34. The method consisting essentially of the steps of claim 1.

35. The method consisting essentially of the steps of claim 19.

36. A lipid composition produced by the method of claim 1, 2, 3, 4, 5, 6, 7, 8, 9, 10, 11, 12, 13, 14, 15, 16, 17 or 18.

* * * * *